US011311628B2

(12) United States Patent
Bigner et al.

(10) Patent No.: US 11,311,628 B2
(45) Date of Patent: Apr. 26, 2022

(54) PRODUCTION OF IMMUNOTOXIN D2C7—(SCDSFV)—PE38KDEL

(71) Applicant: Duke University, Durham, NC (US)

(72) Inventors: Darell D. Bigner, Mebane, NC (US); Vidyalakshmi Chandramohan, Durham, NC (US); Charles Pegram, Durham, NC (US)

(73) Assignee: Duke University, Durham, NC (US)

( * ) Notice: Subject to any disclaimer, the term of this patent is extended or adjusted under 35 U.S.C. 154(b) by 271 days.

(21) Appl. No.: 16/342,914

(22) PCT Filed: Oct. 13, 2017

(86) PCT No.: PCT/US2017/056562
§ 371 (c)(1),
(2) Date: Apr. 17, 2019

(87) PCT Pub. No.: WO2018/075357
PCT Pub. Date: Apr. 26, 2018

(65) Prior Publication Data

US 2020/0046847 A1 Feb. 13, 2020

Related U.S. Application Data

(60) Provisional application No. 62/408,963, filed on Oct. 17, 2016.

(51) Int. Cl.
*A61K 47/68* (2017.01)
*C07K 16/06* (2006.01)
*C07K 16/28* (2006.01)

(52) U.S. Cl.
CPC ........ *A61K 47/6829* (2017.08); *C07K 16/065* (2013.01); *C07K 16/2863* (2013.01); *C07K 2317/31* (2013.01); *C07K 2317/624* (2013.01); *C07K 2317/73* (2013.01)

(58) Field of Classification Search
CPC ............ A61K 47/6829; C07K 2317/73; C07K 2317/624; C07K 16/2863; C07K 2317/31; C07K 16/065
See application file for complete search history.

(56) References Cited

U.S. PATENT DOCUMENTS

| | | | |
|---|---|---|---|
| 6,264,940 | B1 | 7/2001 | Gromeier |
| 6,518,033 | B1 | 2/2003 | Gromeier |
| 8,066,983 | B2 | 11/2011 | Wimmer |
| 2005/0261170 | A1 | 11/2005 | Hansen |
| 2009/0269343 | A1 | 10/2009 | Bigner |
| 2017/0216382 | A1 | 8/2017 | Gromeier |
| 2018/0296614 | A1 | 10/2018 | Bigner |

FOREIGN PATENT DOCUMENTS

| | | | |
|---|---|---|---|
| WO | 2007112047 | A2 | 10/2007 |
| WO | 2012015912 | A1 | 2/2012 |
| WO | 2015/171965 | A2 | 11/2015 |
| WO | 2017066557 | A1 | 4/2017 |
| WO | 2017165266 | A1 | 9/2017 |
| WO | 2018067446 | A1 | 4/2018 |
| WO | 2019195302 | A1 | 10/2019 |

OTHER PUBLICATIONS

Arita, N., et al., Epidermal growth factor receptor in human glioma. J Neurosurg, 1989. 70(6): p. 916-9.
Bao, X. et al. "Antitumor efficacy of D2C7-(scdsFv)-PE38KDEL, a novel immunotoxin targeting EGFRwt and EGFRvIII, by convection-enhanced delivery in orthotopic brain tumor mouse models," Journal for Immunotherapy of Cancer (2013) P126.
Bao, X. et al. "Preclinical toxicity evaluation of a novel immunotoxin, D2C7-(scdsFv)-PE38KDEL, administered via intracerebral convection-enhanced delivery in rats," Investigational New Drugs (2016) 34(2):149-158.
Bartlett, J.M., et al., The prognostic value of epidermal growth factor receptor mRNA expression in primary ovarian cancer. Br J Cancer, 1996. 73(3): p. 301-6.
Brennan, C.W., et al., The somatic genomic landscape of glioblastoma. Cell, 2013. 155(2): p. 462-77.
Brown MC, et al. Oncolytic polio virotherapy of cancer. Cancer. 2014;120(21):3277-3286.
Brown MC, et al. "Cancer immunotherapy with recombinant poliovirus induces IFN-dominant activation of dendritic cells and tumor antigen-specific CTLs." Science translational medicine 9.408 (2017): eaan4220.
Buchner, J. et al. "A Method for Increasing the Yield of Properly Folded Recombinant Fusion Proteins: Single-Chain Immunotoxins from Renaturation of Bacterial Inclusion Bodies," Analytical Biochemistry (1992) 205(2):263-270.
Chaffanet, M., et al., EGF receptor amplification and expression in human brain tumours. Eur J Cancer, 1992. 28 (1): p. 11-7.
Chandramohan, V. et al. "Production and quality control assessment of a GLP-grade immunotoxin, D2C7-(scdsFv)-PE38KDL, for a phase I/II clinical trial," Applied Microbiology and Biotechnology (2016) 101(7):2747-2766.
Chandramohan, V., et al. "Construction of an immunotoxin, D2C7-(scdsFv)-PE38KDEL, targeting EGFRwt and EGFRvIII for brain tumor therapy." Clinical Cancer Research 19.17 (2013): 4717-4727.
Fox, S.B., et al., Prognostic value of c-erbB-2 and epidermal growth factor receptor in stage A1 (Tla) prostatic adenocarcinoma. Br J Urol, 1994. 74(2): p. 214-20.
Frederick, L., et al., Diversity and frequency of epidermal growth factor receptor mutations in human glioblastomas. Cancer Res, 2000. 60(5): p. 1383-7.

(Continued)

*Primary Examiner* — Ruixiang Li
(74) *Attorney, Agent, or Firm* — Quarles & Brady LLP

(57) ABSTRACT

D2C7-(scdsFv)-PE38KDEL (D2C7-IT) is a recombinant *Pseudomonas* exotoxin A-based immunotoxin (IT), targeting both wild-type epidermal growth factor receptor (EGFRwt) and mutant EGFR variant III (EGFRvIII) proteins overexpressed in glioblastomas. A good laboratory practice (GLP) manufacturing process was developed to produce sufficient material for a Phase I/II clinical trial. D2C7-IT was expressed under the control of the T7 promoter in *Escherichia coli* BLR (λ DE31). D2C7-IT was produced by a 10 L batch fermentation process and was then purified from inclusion bodies using anion exchange, size exclusion, and an endotoxin removal process that achieved a yield of over 300 mg of purified protein.

6 Claims, 7 Drawing Sheets

(56) References Cited

OTHER PUBLICATIONS

International Searching Authority, International Search Report and Written Opinion for application PCT/US2017/056562, dated Jan. 12, 2018.
Klijn, J.G., et al., The clinical significance of epidermal growth factor receptor (EGF-R) in human breast cancer: a review on 5232 patients. Endocr Rev, 1992.13(1): p. 3-17.
Libermann, T.A., et al., Amplification, enhanced expression and possible rearrangement of EGF receptor gene in primary human brain tumours of glial origin. Nature, 1985. 313(5998): p. 144-7.
Libermann, T.A., et al., Expression of epidermal growth factor receptors in human brain tumors. Cancer Res, 1984. 44(2): p. 753-60.
Grandis, J.R. et al., Quantitative immunohistochemical analysis of transforming growth factor-alpha and epidermal growth factor receptor in patients with squamous cell carcinoma of the head and neck Cancer, 1996. 78(6): p. 1284-92.
Pavelic, K., et al., Evidence for a role of EGF receptor in the progression of human lung carcinoma. Anticancer Res, 1993.13(4): p. 1133-7.
Seetharam, S., et al., Increased cytotoxic activity of Pseudomonas exotoxin and two chimeric toxins ending in KDEL. J Biol Chem, 1991. 266(26): p. 17376-81.
Weldon, J.E. et al., A guide to taming a toxin—recombinant immunotoxins constructed from Pseudomonas exotoxin A for the treatment of cancer. FEBS J, 2011. 278(23): p. 4683-700.
Wikstrand CJ, et al. Cell surface localization and density of the tumor-associated variant of the epidermal growth factor receptor, EGFRvIII. Cancer Res. 1997;57(18):4130-4140.
Bao, X., et al. “EGFR/EGFRvIII-targeted immunotoxin therapy for the treatment of glioblastomas via convection-enhanced delivery.” Receptors & clinical investigation 3.4 (2016).
Chandramohan, V. et al. “A novel recombinant immunotoxin-based therapy targeting wild-type and mutant EGFR improves survival in murine models of glioblastoma.” Oncoimmunology 2.12 (2013): e26852.
ClinicalTrials.gov. D2C7 for Adult Patients with Recurrent Malignant Glioma. Accessed online at https://web.archive.org/web/20170716200201/https://clinicaltrials.gov/ct2/show/study/NCT02303678. Version dated Jul. 26, 2017.
National Cancer Institute. NCI Drug Dictionary. Immunotoxin D2C7-(scdsFv)-PE38KDEL. Available online at https://www.cancer.gov/publications/dictionaries/cancer-drug/def/immunotoxin-d2c7-scdsfv-pe38kdel. Version accessed dated Apr. 24, 2018.

| Features | Nucleotides |
|---|---|
| T7 Promoter | 5-27 |
| D2C7-(scdsFv) open reading frame | 88-813 |
| PE38KDEL Pseudomonas exotoxin | 815-1869 |
| f1 origin | 2091-2517 |
| CAT (CamR) Chloramphenicol resistance gene | 2985-3643 |
| Co1E1 origin | 3953-4626 |

Merged 29-32
D2C7-IT Q-fractions

PRODUCTION OF IMMUNOTOXIN D2C7—(SCDSFV)—PE38KDEL

This invention was made with government support under 5P01CA154291 awarded by the National Cancer Institute. The government has certain rights in the invention.

TECHNICAL FIELD OF THE INVENTION

This invention is related to the area of production and quality control. In particular, it relates to production and quality control of an anti-cancer immunotherapy agent.

BACKGROUND OF THE INVENTION

The epidermal growth factor receptor (EGFR), a 170-kDa, transmembrane glycoprotein, is a member of the ErbB/EGFR family of receptor tyrosine kinases (RTKs). The overexpression of EGFR is reported in head and neck cancer [1], breast cancer [2], ovarian carcinoma [3], lung cancer [4], prostate cancer [5], and brain tumors [6, 7]. Compared to normal control brain specimens, a 300-fold overexpression of EGFR is observed in glioma [8]. Comprehensive molecular analyses have identified mutation, rearrangement, altered splicing, and/or focal amplification of EGFR in 57% of glioblastoma patients [9]. In the absence of gene amplification, EGFR protein overexpression has also been demonstrated in glioblastoma [10].

The EGFR gene amplification is often associated with gene rearrangements. The most common rearrangement is the EGFR variant III (EGFRvIII) mutant, which is present in 67% of glioblastomas with EGFR amplification [11]. The high prevalence of EGFR fusion and deletion variants in glioblastomas necessitates the development of a therapeutic strategy that will target the different EGFR alterations that exist concurrently in a tumor. An agent targeting multiple variants of EGFR is expected to have a major impact on the survival of glioblastoma patients.

*Pseudomonas* exotoxin A (PE), secreted by *Pseudomonas aeruginosa*, is a potent toxin that can be chemically or genetically fused to monoclonal antibodies (mAbs) or mAb fragments targeting tumor-specific proteins [12]. These mAb-toxin chimeras specifically targeting and eliminating tumor cells are called immunotoxins (ITs). Recombinant ITs are produced by genetically fusing a 38-kDa truncated mutant form of PE, PE38KDEL, to the single-chain variable-region antibody fragments (scFvs), consisting of the heavy- and light-chain variable regions (VH and VL) [13]. D2C7-(scdsFv)-PE38KDEL (D2C7-IT) is a novel recombinant IT with dual specificity for the EGFRwt and mutant EGFRvIII proteins [14]. In preclinical studies, the dual-specific immunotoxin D2C7-IT demonstrated a strong anti-tumor response against intracranial glioblastoma xenografts expressing either EGFRwt (prolonged survival by 310%, P=0.006) or both EGFRwt and EGFRvIII (prolonged survival by 166%, P=0.001) [14]. D2C7-IT is currently in a Phase I/II clinical trial (NCT02303678) for recurrent adult glioblastoma patients.

There is a continuing need in the art to make high quality and high quantity biologicals such as D2C7-(scdsFv)-PE38KDEL.

SUMMARY OF THE INVENTION

According to one aspect of the invention a method produces clinical grade D2C7(scdsFv)-PE38KDEL immunotoxin. An *E. coli* lambda lysogen comprising a plasmid encoding said immunotoxin is cultured in a fermentor to produce a bacterial cell paste. Bacteria of the bacterial cell paste are lysed in a buffer comprising $MgSO_4$, DNaseI, and lysozyme. Inclusion bodies are collected from the lysed bacteria. The inclusion bodies are solubilized and proteins of the solubilized inclusion bodies are reduced to form reduced proteins of the inclusion bodies. The reduced proteins of the inclusion bodies are refolded in the presence of a protease inhibitor to form single-chain disulfide stabilized immunotoxin. The single-chain disulfide stabilized immunotoxin is purified to remove the protease inhibitor and endotoxin to form purified, single-chain disulfide stabilized immunotoxin. The purified single-chain disulfide stabilized immunotoxin is stored at a temperature of −70° to −90° C.

According to another aspect of the invention a sterile preparation of D2C7(scdsFv)-PE38KDEL immunotoxin is provided. The sterile preparation is at least 95% pure as assessed by high performance liquid chromatography. The sterile preparation contains less than 5% aggregates. The sterile preparation contains less than 5% fragments. The sterile preparation contains from 0.05 to 1.5 mg/ml total protein. The sterile preparation is stable for greater than 3 years.

These and other embodiments which will be apparent to those of skill in the art upon reading the specification provide the art with a robust method of making an important clinical biological therapeutic agent.

BRIEF DESCRIPTION OF THE DRAWINGS

(FIG. 2A) pRB 199-D2C7-(scdsFv)-PE38KDEL plasmid map with key features and (FIG. 2B) pRB199-D2C7-(scdsFv)-PE38KDEL plasmid restriction map.

DETAILED DESCRIPTION OF THE INVENTION

Figure 1:
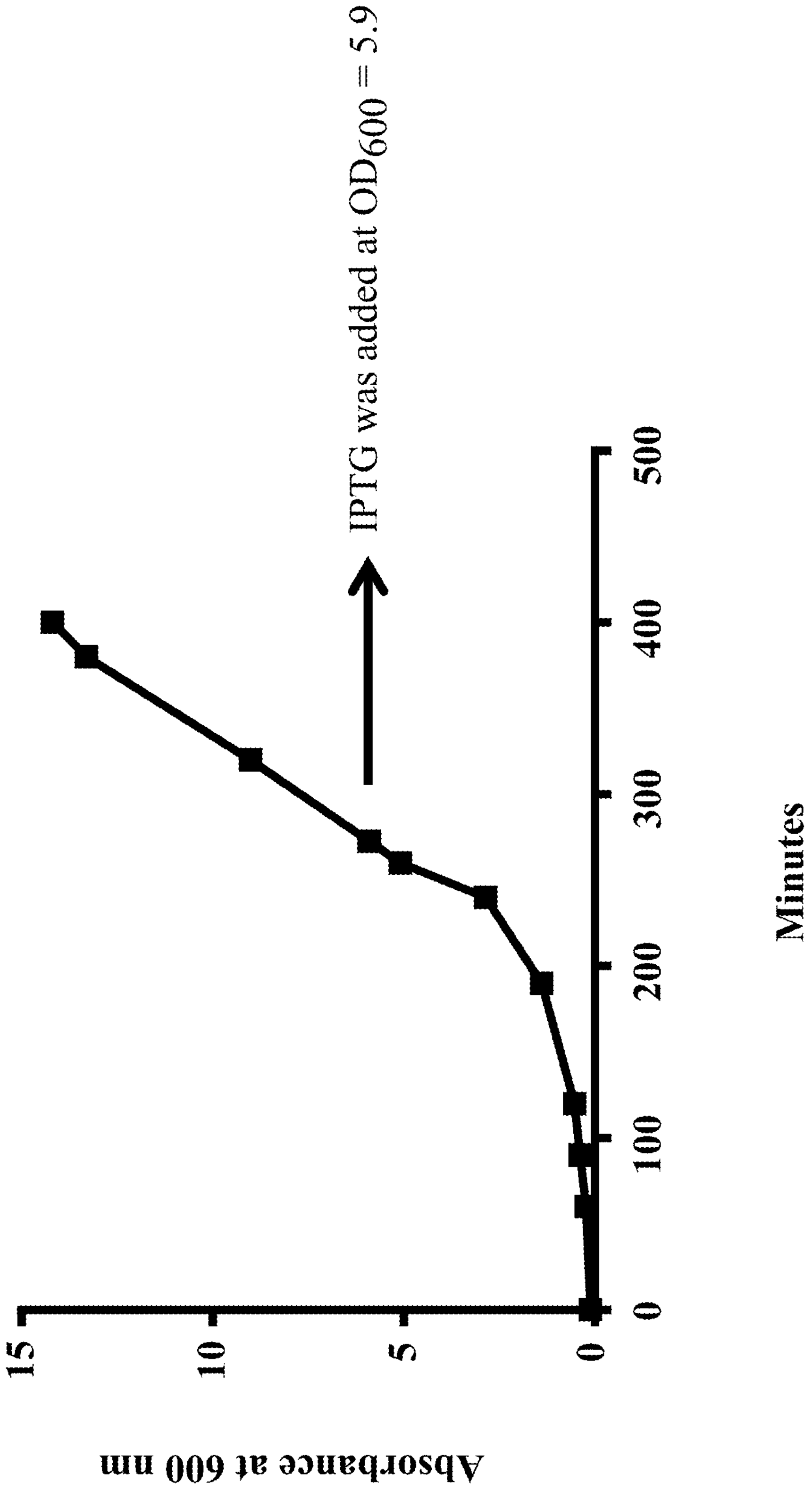
FIG. 1 shows a D2C7-IT fermentation profile. A representative 8L D2C7-IT fermentation profile is shown. The X-axis represents fermentation time in minutes and the Y-axis represents $OD_{600}$ values.

The inventors have developed a highly pure, highly stable preparation of D2C7-(scdsFv)-PE38KDEL immunotoxin. This was accomplished using a method with a number of features which overcame difficulties encountered. These are described in detail below.

The inventors have successfully manufactured a GLP grade D2C7-(scdsFv)-PE38KDEL immunotoxin for a Phase I/II clinical trial in patients with recurrent glioblastomas (NCT02303678, D2C7 for Adult Patients with Recurrent Malignant Glioma, clinicaltrials.gov). High level of expression of D2C7-IT in *E. coli* resulted in aggregation of the expressed protein molecules into inclusion bodies. From a total of nine fermentation runs we generated a total of 26.3 gm of inclusion body. Solubilization of D2C7-IT inclusion body was achieved using high concentration of Guanidine-HCl which was then refolded by removal of solubilization agent through dilution in refolding buffer. Twenty six grams of the D2C7-IT inclusion body was refolded by dilution in a total of 260 L of refolding buffer. Refolded D2C7-IT was dialyzed and then purified through a strong anion-exchange chromatographic step followed by a size exclusion chromatographic step. The total yield of purified D2C7-IT after anion exchange and size exclusion chromatographic steps were 926.9 mg and 356.2 mg, respectively. Because of the use of bacterial expression system the D2C7-IT protein preparation has endotoxin contamination which requires multiple washes with detergent to remove the majority of this contaminant before polishing on secondary chromatography columns and endotoxin removal resins. The total D2C7-IT after endotoxin removal was 341.96 mg and the final yield of GLP grade D2C7-IT after dialysis against DPBS CTS was 307.75 mg. As discussed and agreed upon with the Food and Drug Administration (FDA) at our pre-IND meeting, the final purified bulk product was made by combining purified intermediate bulk lots 212033, 212034, and 212035 which was subjected to extensive analytical release testing both pre and post vialing.

A quantitative acceptance criterion, with an upper and lower limit, for the potency assay (cytotoxicity assay) used for release and stability testing of the final purified bulk product (Lot 212041) and the final vialed product (Lot 211131) was determined by a statistician. The conclusions are as follows: 1) Final Purified Bulk (Lot 212041) on A431p cells: based upon four available $IC_{50}$ observations, with a mean=40 and SD=7.39, 68% Prediction Interval: 32.7, 47.4. 2) Final Vialed Product (Lot 211131) on A431p cells: based upon 104 IC50 observations, with a mean=40.35 and SD=14.26, 68% prediction interval: 26.1, 54.4. 3) Final Purified Bulk (Lot 212041) on NR6M cells: based upon four available Icso observations, with a mean=306.3 and 80=114.1, 68% Prediction Interval: 192.2, 420.4. 4) Final Vialed Product (Lot 211131) on NR6M cells: based upon 40 $IC_{50}$ observations, with a mean=432.9 and SD-161.4, 68% Prediction Interval: 271.5, 594.3, Upon the request from FDA following the pre-IND comments SDS-PAGE and IEF-Gel analyses were added to the stability testing protocol of the final vialed product (Lot 211131). These additional tests were added to the ongoing stability protocol at the 9-month time point. Therefore, data for these two tests were reported in stability results summary Table IV beginning at 9-months of stability testing. Additionally, upon consultation with the Duke Translational Medicine Institute Regulatory Affairs group the expiry date of the final vialed product (Lot 211131) was extended from 48 months to 60 months after the completion of the 42-month stability testing. Similarly, the expiry date of the final vialed product (Lot 211131) will be extended from 60 months to 72 months after the completion of the 66-month stability testing.

Clinical supply of large quantities of immunotoxins such as D2C7-IT is highly desirable and this protein typifies single chain disulfide stabilized immunotoxins in that it was challenging to produce D2C7-IT at higher yield and purity under GLP conditions. The main difficulty that we encountered during the manufacturing process was the degradation of D2C7-IT when stored at 4° C. in the absence of carrier protein. We had to forego three fermentation batches (Lots 212019, 212020, and 212021) after Q-Sepharose purification due to D2C7-IT degradation at 4° C. We overcame this problem by storing intermediate purification products at −80° C. Despite these challenges, we were able to produce 307.75 mg of GLP grade D2C7-IT from a total of nine, 8 L fermentation runs. Most importantly, this material is currently being tested in a Phase I/II clinical trial in patients with recurrent glioblastomas and we anticipate that it will save patient's lives.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods

Production of D2C7-IT was performed by the Antibody Engineering and Antibody Therapeutics (AEAT) Program personnel at the Duke University Medical Center AEAT Production Facility. All materials were purchased at the highest purity possible and certificates of analysis from different manufacturers were retained. All equipment was cleaned and tested in accordance with GLP guidelines. All of the AEAT Program personnel were trained on and followed the GLP guidelines during production of the clinical grade D2C7-IT.

D2C7-IT Strain Construction

Plasmid (pRB199-D2C7-scdsFv-PE38KDEL) expressing D2C7-IT has been previously described [14]. The pRB199-D2C7-scdsFv-PE38KDEL plasmid was transformed into the expression host *E. coli* BLR (2 DE3) (Novagen-EMD Millipore, Billerica, Mass.) and positive clones were selected by chloramphenicol resistance. Ten colonies were picked and inoculated into tubes (11CT-20CT) containing 3 ml LB with 75 ng/ml chloramphenicol and 12.5 ng/ml tetracycline. All clones were incubated overnight at 37° C. in a rotary shaker at 250 revolutions per minute (rpm). Two hundred microliters of clones 11CT-20CT were seeded into tubes with 3 ml of Turbo Prime-olate media (Athena Environmental Sciences, Inc., Baltimore, Md.) with chloramphenicol and tetracycline and incubated at 37° C. in a rotary shaker at 250 rpm. After 2 hours of incubation, 3 ml of 40% glycerol was added to all the tubes and six-1 ml aliquots were stored frozen at −80° C. (Accession Cell Bank [ACB] clones). One frozen ACB vial of cells per clone was thawed and 300 nl of the bacterial stock was added to a tube containing turbo prime-olate media with chloramphenicol and tetracycline and incubated for 6 hours at 37° C. in a rotary shaker at 250 rpm. Cultures were induced with 1 mM isopropyl (5-D-thiogalactoside (IPTG) overnight at 37° C. in a rotary shaker at 250 rpm and inclusion body pellets were analyzed in a NuPage 4-12% Bis-Tris gels (Thermo Fisher Scientific, Waltham, Mass.) for protein expression.

Production of D2C7-IT Master Cell Bank

One ACB vial of clone 18CT (DsD2C7-PE38-KDEL Clone 18CT BLR[DE3]) was thawed into 25 ml of Animal Product Free Terrific Broth media (Teknova, Hollister, Calif.) and incubated in a rotary shaker overnight at 250 rpm at 37° C. The following day, 25 ml of the overnight culture of clone 18CT was added to 150 ml of fresh Animal Product Free Terrific Broth media and incubated in a rotary shaker at 250 rpm at 37° C. until the $OD_{600}$ was 0.845. Master cell bank (MCB) vials of D2C7-IT (DsD2C7-PE38-KDEL MCB of clone 18 in *E. coli* BLR[DE3] 3-1312) were prepared by combining 800 μl of clone 18CT bacterial culture with 200 μl of 100% glycerol per vial.

The following quality control testing of the D2C7-IT MCB was performed by Charles River Biopharmaceutical Services, Malvern, Pa.; Pennsylvania State University-Gastroenteric Disease Center, University Park, Pa.; and Genewiz, South Plainfield, N.J.:

1. Bacterial purity: The purity of the D2C7-IT MCB microbial culture was determined through growth in differential agars, viability testing of microbial suspension, and gene copy number analysis by amplification of specific nucleic acids utilizing fluorescent probes (Charles River Biopharmaceutical Services).
2. Bacterial identity: The strain of *E. coli* used for MCB production was verified through pulse field gel electrophoresis (Pennsylvania State University), comparative sequence analysis of genomic DNA encoding Gyrase B, and retention of selectable markers in transformed host cell lines (Charles River Biopharmaceutical Services).
3. Plasmid identity: Identity of the transformed pRB199-D2C7-scdsFv-PE38KDEL plasmid was confirmed through the retention of the recombinant construct in transformed *E. coli* cell lines, restriction endonuclease analysis of the plasmid DNA by agarose gel electrophoresis and ethidium bromide staining (Charles River Biopharmaceutical Services), and isolation and sequencing of the pRB199-D2C7-(scdsFv)-PE38KDEL plasmid from the master cell bank by Genewiz (South Plainfield, N.J.).
4. Safety: The safety of the MCB was established by the testing for Shiga-like toxin/toxin genes (Pennsylvania State University), the induction of bacterial virus from *E. coli* using Mitomycin C, and the ultrastructural evaluation of fluid samples for bacteriophage particles by negative staining (Charles River Biopharmaceutical Services).

D2C7-IT Fermentation

One frozen MCB vial was thawed and 0.2 mL of bacterial cells were inoculated into 2.0 ml of SOC media and incubated for 2 hours at 220 rpm and 37° C. The cells were then plated on ten LB-chloramphenicol (75 (μg/ml) plates and incubated at 37° C. overnight. The ten plates of grown bacteria were inoculated into two 2-L shake flasks, each containing 500 mL of sterile, prepared Animal Product Free Terrific Broth media (Teknova) supplemented with 4.1 mM $MgSO_4$, 0.5% glucose, and chloramphenicol at 34 μg/mL. The inoculated seed flasks were incubated at 230 rpm and 37° C. When the optical density at 600 nm ($OD_{600}$) of seed culture reached an $OD_{600}$ 1, both the seed flasks were pooled to yield a 12.5% inoculum for the fermentor, A 10-L fermentor was prepared for fermentation of the D2C7-IT by batching the fermentor with 7-L of Terrific Broth media, 2% glucose, 0.05% magnesium sulfate, and 34 μg/mL chloramphenicol. The final volume in the fermentor was 8 L. The fermentor was set to culture parameters as follows: Agitation: cascade; Temperature: 37° C. (36.5-37.5° C.); pH: 7.07.2; Dissolved Oxygen:—70%; Antifoam: as required. The prepared media in the fermentor was inoculated with the prepared D2C7-IT seed culture. The D2C7-IT fermentation culture was sampled hourly for $OD_{600}$ measurement. D2C7-IT expression was induced with 1 mM IPTG for 2 h when the $OD_{600}$ reached 6±1. Cells were harvested by centrifugation and the paste was stored at −20° C. overnight or until lysis.

Inclusion Body Preparation

Thawed cell paste (30 gm each) was resuspended in 100 mL of 50 mM Tris-HCl pH 7.5 buffer and dispersed through homogenization. Next, 0.5 mL of 1M $MgSO_4$ (5 mM final concentration), 6000 units of DNase I, and 300 mg of Lysozyme (10 mgs/gm bacterial pellet) were added to the dispersed cell mixture and incubated at room temperature for 1 hour. Twelve mL of 5M NaCl (500 mM final concentration) and 9.6 mL of 25% Triton X-100 buffer (2% final concentration) were added to the bacterial lysate, which were then homogenized and incubated at room temperature for 30 minutes. Finally, 4 mL of 0.5M EDTA (16.7 mM final concentration) was added to the bacterial lysate and the final volume was adjusted to 200 mL with 2% Triton-X 100 in TE 50/20 buffer (50 mM Tris-HCl pH 7.5 and 20 mM EDTA), dispersed thoroughly by homogenization, and centrifuged at 10,000 rpm at 4° C. for 50 min. The bacterial pellets were washed (200 mL total volume) twice with 2% Triton-X 100 in TE 50/20 buffer and three times with TE 50/20 buffer. During each wash step, the bacterial pellet was thoroughly dispersed through homogenization followed by centrifugation, at 10,000 rpm at 4° C. for 50 min. The final inclusion body pellets were labeled and stored at −20° C. until solubilization.

Inclusion Body Solubilization and D2C7-IT Refolding

Individual inclusion body pellets were dissolved in solubilization buffer (6M Guanidine-HCl) overnight at room temperature on a shaker. The solubilized inclusion body was centrifuged at 16,000 rpm at 4° C. for 50 min. The resulting supernatant was collected and the protein concentration was determined by Pierce Coomassie Plus (Bradford) Assay Kit (Thermo Fisher Scientific). The solubilized inclusion body was then diluted to a concentration of 10 mg/mL using an appropriate volume of the solubilization buffer. Solubilized D2C7-IT was then reduced by the addition of dithioerythritol (DTE; Sigma, St. Louis, Mo.) to 10 mg/mL for the final concentration and incubated for 16 h at room temperature with gentle shaking. Reduced D2C7-1T was slowly diluted 100-fold into refolding buffer (100 mM Tris-HCl pH 8.0, 0.5 M L-arginine-HCl, 0.9 mM oxidized form of glutathione, 2 mM EDTA, 2 ml of Protease Inhibitor/L [Sigma]; pH 10.3) with gentle mixing. The refolding reaction was allowed to proceed for 72 hours at 2-8° C. without agitation.

Dialysis, Filtration, and Purification of D2C7-IT

The refolded protein solution (3-5 L) was dialyzed against 50 liters of dialysis buffer (100 mM Urea, 20 mM Tris-HCl, pH 7.5) overnight at 2-8° C. The dialyzed retentate was filtered through a 0.22 jam bottle top filter for subsequent purification.

A High Resolution (HR16/10) column (GE Healthcare) was packed with Q-Sepharose High Performance (HP) anion exchange resin (GE Healthcare) and had a packed bed volume of 20 mL. The Q Sepharose HP column was equilibrated with ten column volumes (CVs) of Buffer A (20 mM Tris-HCl, pH 7.5) until the conductivity of the effluent was within 2 mS/cm of the equilibration buffer. The column was then run at a flow rate of 6 mL/min. The D2C7-IT Q-Sepharose HP Load (4-6 L of dialyzed and filtered protein solution) was applied to the Q-Sepharose HP column, and the flow-through was collected. After washing Q-Sepharose HP column with five CVs of Buffer A (20 mM Tris-HCl, pH 7.5), the D2C7-IT was eluted (flow rate, 6 mL/min/fraction; total runtime, 60 min) using a linear gradient of Buffer B (20 mM Tris-HCl, pH 7.5, 1M NaCl), with tubes 1-10 collecting fractions with 0-10% buffer B, tubes 11-50 collecting fractions with 10%-50% buffer B, and tubes 51-60 collecting fractions with 50%-100% buffer B, respectively. The main D2C7-IT-containing fractions eluted from Q-Sepharose HP chromatography were pooled based on SDS-PAGE analysis and processed for High Performance Liquid Chromatography-Size Exclusion Chromatography (HPLC-SEC) purification.

Pooled Q-Sepharose D2C7-IT Q-Sepharose fractions were concentrated using a 30 kDa molecular weight cut-off (MWCO) Vivaspin 20 ultrafiltration device (Sartorius, Bohemia, N.Y.). Pooled D2C7-IT fractions were concentrated to approximately 4 to 6 mg/mL and dialyzed (using autoclaved Spectra/Por 25 kDa MWCO dialysis tubing) overnight against filter sterilized (VacuCap filters, Pall Corporation, Port Washington, N.Y.) endotoxin low TSK buffer (70 mM $Na_2HPO_4$, 62.5 mM $NaH_2PO_4$, and 100 mM $Na_2SO_4$, pH 6.7), which was prepared using sterile intravenous injection water. Dialyzed D2C7-IT was then filtered through a 0.2 m Millex GV filter (EMD Millipore) and run on a TSKgel SuperSW3000 (particle size 4 um, 21.5 mm×30 cm; Tosoh Bioscience, King of Prussia, Pa.) gel filtration column equilibrated with TSK buffer. The column was run at a flow rate of 2 mL/min (total runtime 60 min) and when a stable base line was obtained, a 1 mL D2C7-1T sample was injected and 30-second fractions were collected under sterile conditions. The main D2C7-IT-containing fractions eluted from the TSKgel SuperSW3000 gel filtration column were pooled based on SDS-PAGE analysis, concentrated, and filtered through a 0.2 µm Millex GV filter for endotoxin removal.

A 1×10 cm Econo-Column chromatography column (Biorad, Hercules, Calif.) was packed with ActiClean Etox resin (Sterogene, Carlsbad, Calif.). The column was equilibrated with 10 CVs of IN NaOH and incubated over night at 4° C. The column was then rinsed with 20 CVs of sterile intravenous injection water and equilibrated with 5 CVs of TSK buffer (filtered through 0.2 jam Acrodisc Units with Mustang E Membrane for endotoxin removal; Pall Corporation). Concentrated D2C7-IT was passed over the ActiClean Etox column at a flow rate of 1 mL/min for endotoxin removal. The D2C7-1T eluate from the ActiClean Etox column was then dialyzed overnight at 4° C. against Cell Therapy Systems DPBS CTS without Calcium Chloride without Magnesium Chloride (Thermo Fisher Scientific). Purified individual bulk lots of D2C7-IT were transferred to 50 mL conical tubes, labeled, and stored at −80° C.

Preparation of Final Purified Bulk D2C7-IT Product

The final purified bulk product was made by combining purified intermediate bulk lots. Individual purified intermediate bulk lots were filtered through a 0.2 m Millex GV filter and combined into one purified bulk lot. The protein concentration of the bulk lot was assessed by Pierce Coomassie Plus (Bradford) Assay and the volume was adjusted to yield a final concentration of approximately 120 µg/mL using DPBS CTS pH 7.4.

D2C7-IT Analytical Release Testing

The analytical tests performed on the final purified bulk D2C7-IT product for release to Compounding Pharmacy for vialing are described below.

Color, Appearance, and Clarity by Visual Inspection

The final purified bulk D2C7-IT product was assessed by visual inspection to determine if the soluble product in the liquid formulation was free from any particulate matter, opaqueness, and/or tint or turbidity of the solution.

Identity by SDS-PAGE

SDS-PAGE (non-reduced and reduced) analysis was performed using NuPAGE Novex 4-12% Bis-Tris pre-cast polyacrylamide gels (Thermo Fisher Scientific) to estimate the molecular weight and identity of the final bulk D2C7-IT product. The final bulk D2C7-IT product ran on NuPAGE gel was visualized by staining with GelCode Blue Stain Reagent (Thermo Fisher Scientific). Molecular weight standards (Precision Plus Protein Dual Color Standards; Bio-Rad) were included on the same gel in order to determine the molecular weight of the purified bulk product through relative electrophoretic mobility comparison with that of the standards.

Protein Concentration by Pierce Coomassie Plus (Bradford) Assay

Pierce Coomassie Plus (Bradford) Assay was used to determine the protein concentration of the final purified bulk D2C7-IT product. Bovine Serum Albumin (BSA) was used to prepare a known protein concentration reference standard in the same diluent as the final purified bulk D2C7-IT product. Diluted standards and the D2C7-IT sample were added to the Pierce Coomassie Plus reagent, incubated at ambient temperature for 5-10 minutes, and the optical density of the samples were measured at 595 nm in a spectrophotometer. The protein concentration of the final purified D2C7-IT product was determined using the BSA reference standard curve.

Potency Testing by Cytotoxicity in NR6M and A431P Cell Lines

The cytotoxic activity of the final purified bulk product was determined using the CellTiter-Fluor Cell Viability assay reagent (Promega, Madison, Wis.). The A431P (epidermoid carcinoma cell line expressing EGFRwt) and NR6M (Swiss 3T3 mouse fibroblast cell line transfected with the EGFRvIII) cells were cultured in Ix Zinc Option (ZO) medium (Thermo Fisher Scientific) supplemented with 10% fetal bovine serum. Cells were trypsinized, washed with 1×PBS and counted with a hemocytometer. The cells were then seeded in 96-well plates at $5×10^3$ (A431P) and $5*10^4$ (NR6M) cells/well in 100 p.l of the growth medium and incubated at 37° C., 5% CO2 overnight. The final purified bulk D2C7-IT product was diluted in 1×PBS-0.2% BSA and was added to the wells at an initial concentration of 1000 ng/mL, followed by 10-fold serial dilutions. The plates with A431P and NR6M cells were incubated at 37° C. and 5% CO2 for an additional 48 h. After the 48 h incubation period, CellTiter-Fluor Reagent (100 µL/well) was added and the plates were incubated for 70 mins at 37° C. and 5% CO2. The plates were then read at 400 nm-Excitation/505 nm-Emission. The data were analyzed using GraphPad Prism 4 software. The $OD_{600}$ values were averaged for the cells that were left untreated. One half of this average was considered the 50% growth inhibition value. The concentration of the purified bulk D2C7-IT corresponding to the 50% growth inhibition value was reported as the IC50 value.

Purity by HPLC-SEC

A TSKgel SuperSW3000 gel filtration column connected to a Beckman Coulter Gold high performance liquid chromatography (HPLC) system with pump module 126, detector module 168, and 32 Karat software was utilized to assess the purity of the final bulk D2C7-IT product. The purified bulk D2C7-IT protein (12 jig) was injected into the SuperSW3000 size exclusion chromatography (SEC) column. The eluate from the column was analyzed through a detector, and the absorbance (at 280 nm) was measured and used to create a chromatogram. From the area of the peak on the chromatogram, the percentages of the bulk D2C7-IT protein, aggregates, and cleavage fragments in the final product were determined.

Purity by Isoelectric Focusing

The purity of the final bulk D2C7-IT product was determined through isoelectric focusing (IEF). The isoelectric point (pi) of the bulk D2C7-IT was determined using Novex pH 3-10 IEF Protein Gels (Thermo Fisher Scientific), and the IEF Marker 3-10 (Thermo Fisher Scientific) was used as a reference standard.

DNA Content (Residual *E. coli* DNA)

The purity of the final bulk D2C7-IT product was determined through quantitation of residual *Escherichia coli* (*E. coli*) DNA in the final purified bulk D2C7-IT product (Charles River Laboratories, Malvern, Pa.), Quantitative fluorescent PCR (QF-PCR) was used to detect the presence and quantity of residual *E. coli* DNA in the final purified bulk D2C7-IT product.

pH

The safety of the final purified bulk product was established through pH measurement. A Accumet AR-15 pH meter (Fisher Scientific) was calibrated using pH 4.0, 7.0, and 10.0 standard buffers. The probe was rinsed and blotted dry before determining the pH of the purified bulk D2C7-IT sample.

Endotoxin Testing

A bacterial endotoxin assay was performed on the final purified bulk D2C7-IT product by the Duke University Hospital Radiopharmacy Laboratory. Endotoxin levels in the purified bulk D2C7-IT product were assessed through the Endosafe-PTS (Charles River Laboratories) test system, utilizing an FDA-licensed disposable Endosafe-PTS test cartridge with a handheld spectrophotometer.

Sterility

Sterility testing on the final purified bulk D2C7-IT product was performed by the Duke University Hospital Radiopharmacy Laboratory. The final purified bulk D2C7-IT sample (0.5 mL) was aseptically added to the BBL Thioglycollate tube and incubated at 30-35° C. for 14 days.

The BBL Trypticase Soy Broth tube was inoculated with 0.5 mL of bulk D2C7-IT sample and incubated at 20-25° C. for 14 days. Media was validated for the ability to grow test organisms and was determined to be sterile prior to use. Both the test and negative control tubes were examined for turbidity at specified intervals during the 14-day test period.

Chloramphenicol Content

Chloramphenicol content was determined by Toxicology Associates, Inc. (Columbus, Ohio), according to the standard gas chromatograph mass spectrometry (GC/MS) detection method. Chloramphenicol is a broad spectrum antibiotic that was extracted with a buffer and a solvent, and derivatized with N,O-Bis(trimethylsilyl)trifluoroacetamide (BSTFA) with 1% trimethylchlorosilane (TCMS) and shot in GC/MS.

IPTG Content

Isopropyl β-D-1-thiogalactopyranoside (IPTG) content was determined by Toxicology Associates, Inc. (Columbus, Ohio), according to the standard GC/MS detection method. IPTG was extracted with a solvent and a buffer, and derivatized with N-Methyl-N-trimethylsilyltrifluoroacetamide (MSTFA) at 70° C. for 20 min, and shot in GC/MS.

Vialing of the Final Purified Bulk D2C7-IT Product

The final purified bulk D2C7-IT product was sent to the Compounding Pharmacy at Duke University Medical Center for vialing. One mL of the final purified bulk D2C7-IT product, at a concentration of 120 μg/mL, was aliquoted into a 2 mL amber, serum type 1 μlass vial with gray butyl Teflon-faced straight plug stoppers, and sealed with center disc tear-out aluminum. Sealed vials were affixed with a label designating the lot number and storage conditions, and stored at −70° C. to −80° C. The final vialed D2C7-IT product was subjected to a product inspection, in which we examined the condition of the straight plug stoppers, the aluminum center disc, and the uniformity of the fill volume. We also checked for any cracks, verified that the product was appropriately labeled, and confirmed that the labels were securely applied. Finally, we ran another round of analytical release testing similar to the testing of the final purified bulk product (with the exception of *E. coli* DNA, chloramphenicol, and IPTG content assessments).

Stability Testing of the Final Vialed D2C7-IT Product

Stability testing of the final vialed D2C7-IT product is being conducted under Protocol 2012-001 over a 5-year duration, from November 2012 to November 2017, by the DUMC/AEAT program. Stability testing includes visual inspection, identity by SDS-PAGE, and verification of protein concentration, purity, potency, and pH (as described earlier), and will be tested at 0, 3, 6, 9, 12, 18, 24, 30, 36, 42, 48, 54, and 60-month time points. Sterility testing will be performed annually.

Example 2

D2C7-IT Master Cell Bank Production and Validation

The *E. coli* strain BLR(DE3) was transformed with the pRB199-D2C7-(scdsFv)-PE38KDEL plasmid. On the basis of chloramphenicol and tetracycline resistance, ten positive clones labelled 11CT-20CT were selected for the screening of D2C7-IT expression. The culture identified as Clone 18CT demonstrated highest levels of D2C7-IT expression (data not shown) and was selected as the source of the D2C7-IT ACB (dsD2C7-PE38-KDEL Clone 18CT BLR [DE3]).

From the D2C7-IT ACB, 240 MCB vials of D2C7-IT Lot 212001 (dsD2C7-PE38-KDEL MCB of clone 18 in *E. coli* BLR[DE3] 3-13-12) were prepared and stored frozen at −80° C.

Figure 2A:
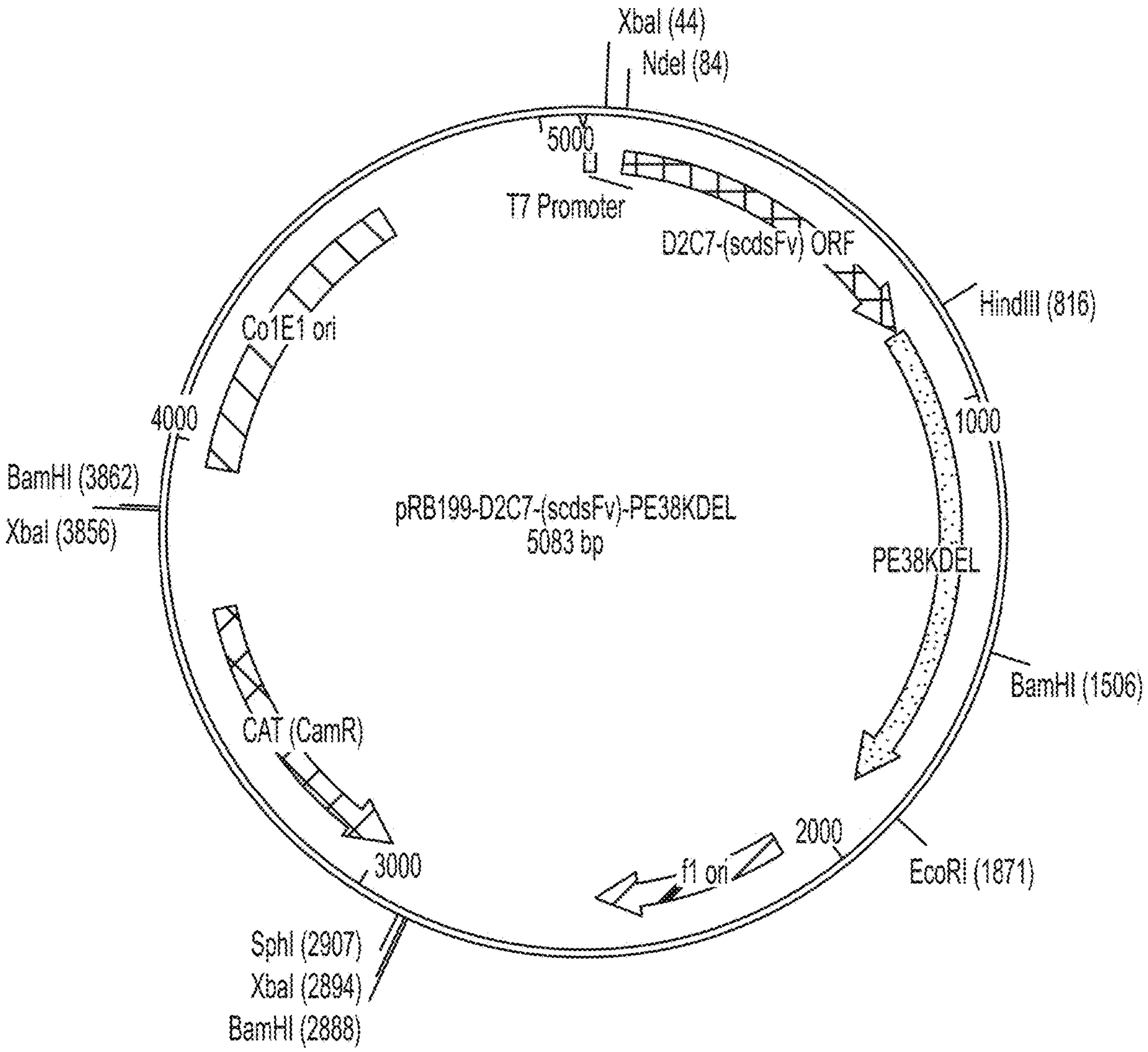
FIGS. 2A-2B show pRB 199-D2C7-(scdsFv)-PE38KDEL plasmid map.
Figure 2B:
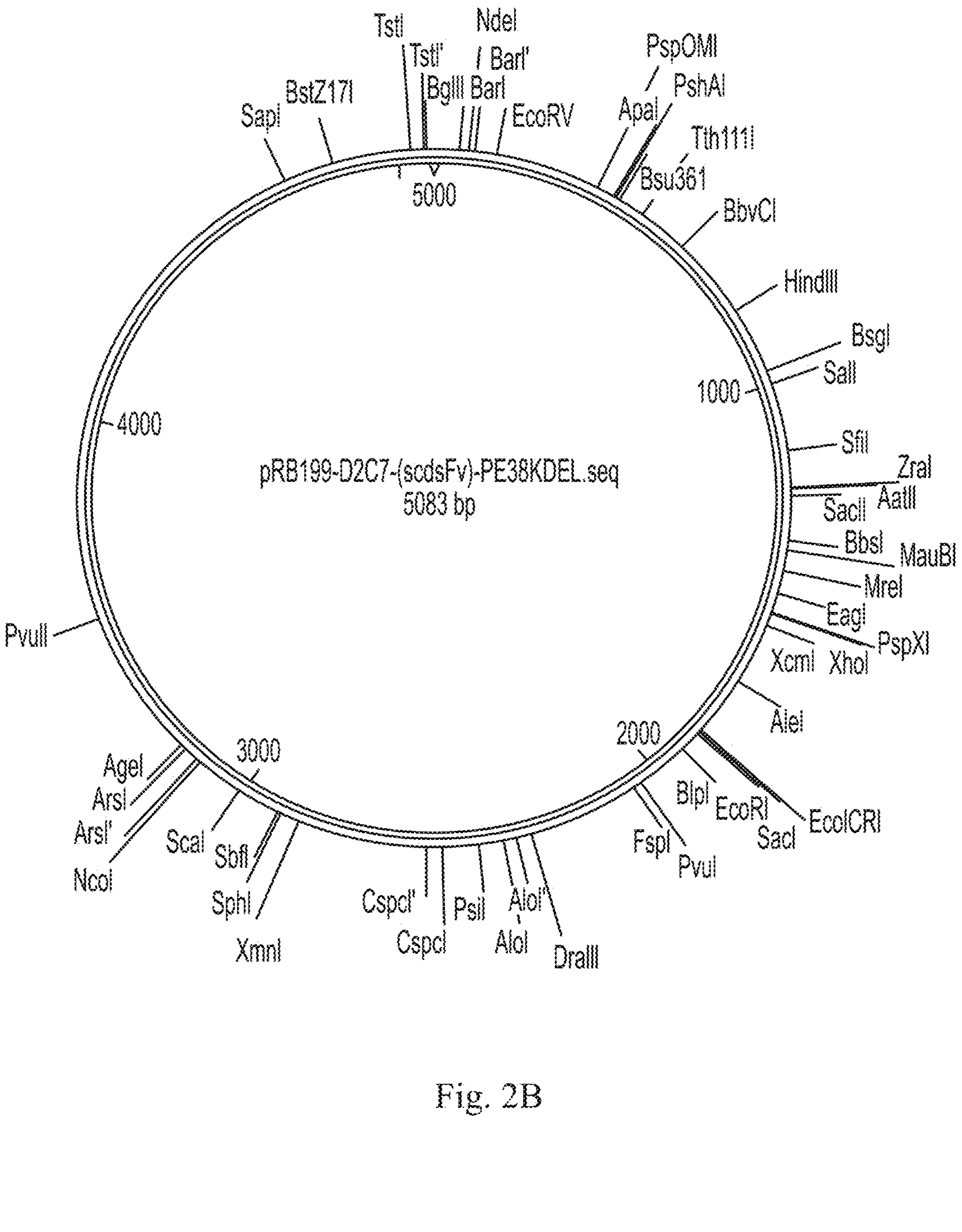

Quality control assessment of D2C7-IT MCB Lot 212001 confirmed the identity of the bacteria to be non-toxic *E. coli* strain BLR(DE3) by comparative sequence analysis of genomic DNA (99.83%), by PFGE (>94% similarity), and through retention of the selection marker chloramphenicol. A sample of the pRB199-D2C7-(scdsFv)-PE38KDEL MCB (Lot 212001) was sequenced and was demonstrated to have 100% identity to the reference sequence. The sequencing data was used to derive the plasmid map and restriction enzyme map included in FIGS. 2A and 2B. Plasmid identity was also confirmed through 100% retention of the pRB 199-D2C7-(scdsFv)-PE38KDEL construct in transformed *E. coli* strain BLR(DE3) and by generation of predicted fragment sizes upon restriction endonuclease digestion;

NdeI (linear): 5151 base pairs (bp); NdeI and EcoRI: 2 fragments—3410 and 1883 bp; NdeI and HindIII: 2 fragments—4727 and 800 bp. Purity of the MCB bacterial culture was established through the absence of contaminating bacterial growth in differential agar, ability of MCB to form viable colonies on LB-agar plates with a viability of $1.2\times10^8$ CFU/mL, and the bacterial copy number pretest of the plasmid digest produced positive amplification of the gene of interest with fluorescent probes (306 plasmid copies/genome equivalent). Finally, the safety of the MCB was established by demonstrating the absence of Shiga-like toxin/toxin gene, absence of bacterial virus through plaque formation assay, and the absence of particles with bacteriophage morphology through negative staining and transmission electron microscopy examination.

Example 3

Fermentation and Purification of Bulk D2C7-IT

Figure 3A:
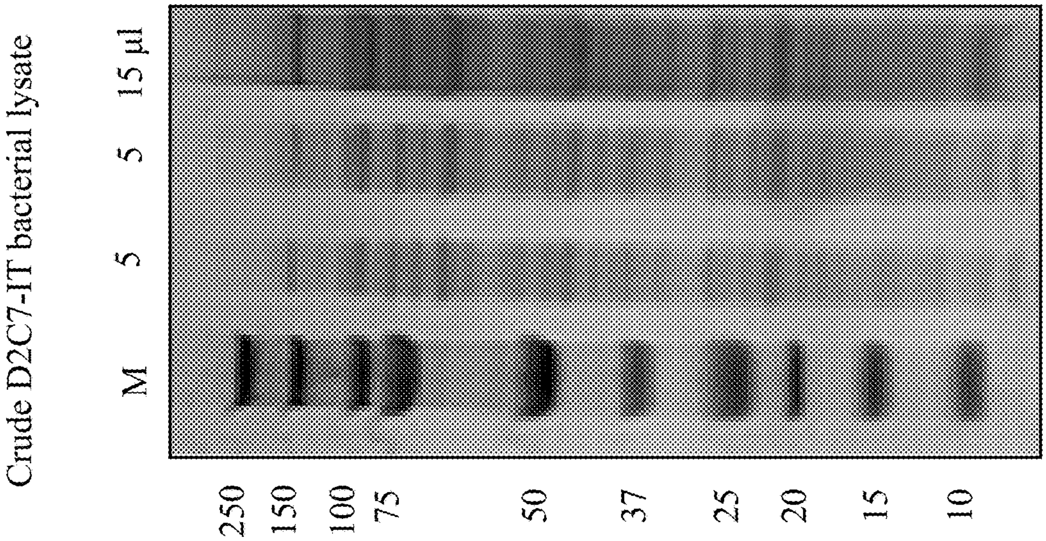
FIGS. 3A-3B show representative Coomassie-stained SDS-PAGE gel of crude D2C7-IT bacterial lysate and purified D2C7-IT inclusion body, (FIG. 3A) *E. coli* BLR (DE3) cells transformed with pRB199-D2C7-(scdsFv)-PE38KDEL were grown in fermentor until $OD_{600}$ reached around 6-8 and the D2C7-IT expression was induced with 1 mM IPTG for 2 h. Samples were harvested at the end of the induction period and different volumes (5 and 15 µl) of crude bacterial lysate was analyzed in a SDS-PAGE gel. M: molecular weight standard, (FIG. 3B) 25 µl of the D2C7-IT inclusion body was analyzed in a SDS-PAGE gel during the final TE 50/20 buffer wash. M: molecular weight standard and IB: inclusion body.
Figure 3B:
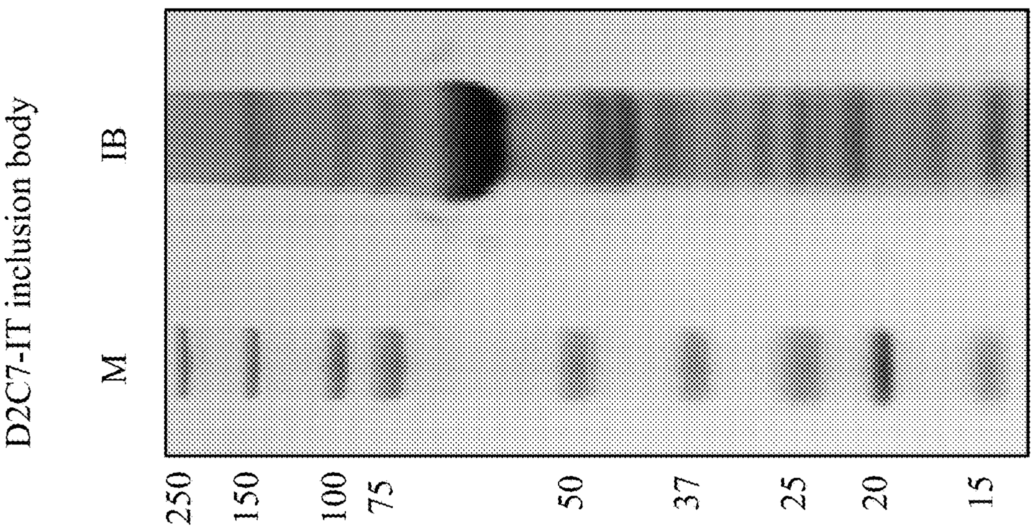
Figure 4A:
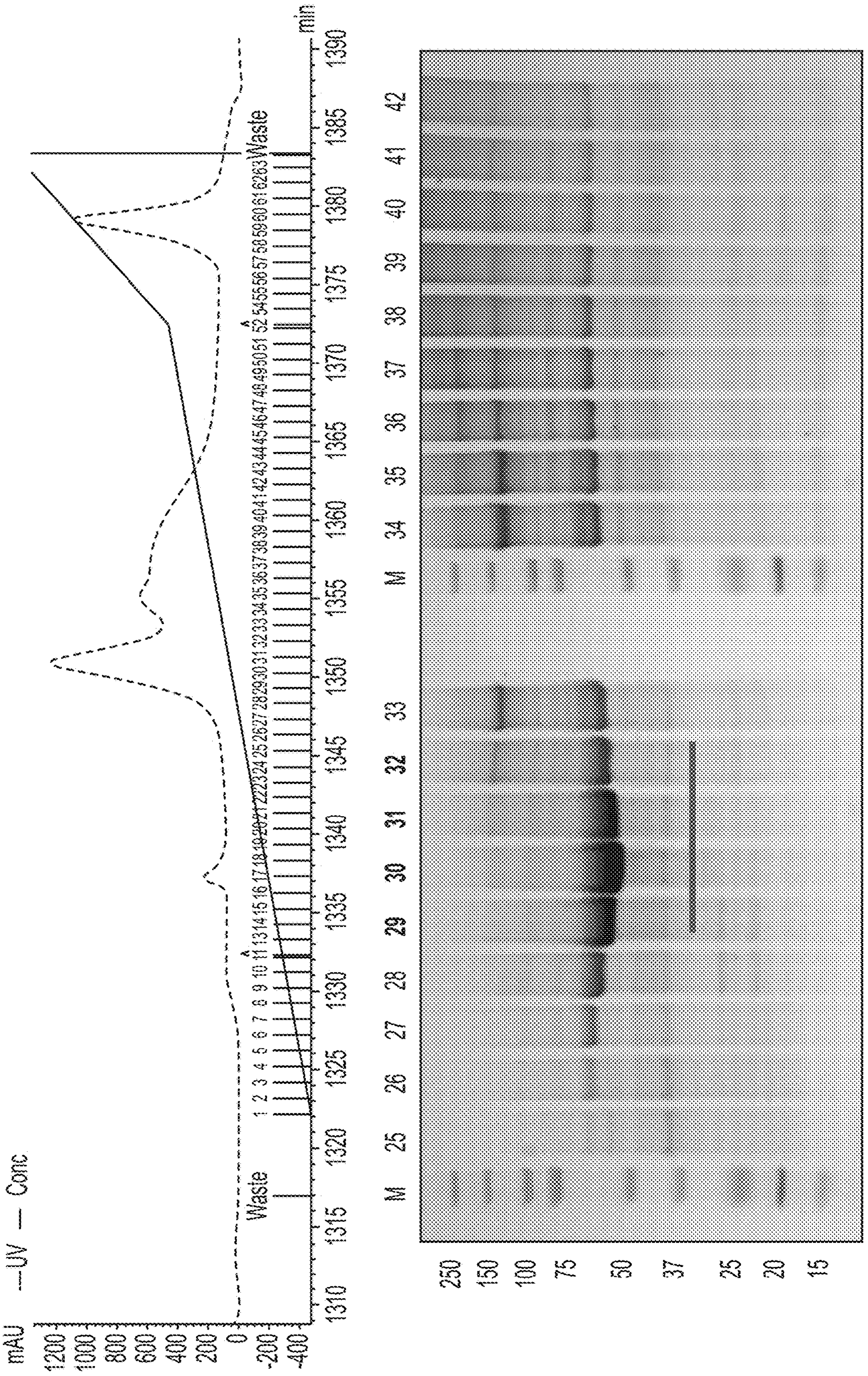
FIGS. 4A-4B show representative chromatographic profile and Coomassie-stained SDS-PAGE gel of D2C7-IT Q-Sepharose fractions, (FIG. 4A) Chromatographic profile of D2C7-IT eluate from the Q-Sepharose FF column. 30 µl of the D2C7-IT eluate fractions 25-42 from the Q-Sepharose FF column was analyzed in a SDS-PAGE gel. M: molecular weight standard, (FIG. 4B) 20 µl of the pooled D2C7-IT Q-Sepharose fractions 29-32 was analyzed in a SDS-PAGE gel. M: molecular weight standard and MQ: merged Q-Sepharose fractions 29-32.
Figure 4B:
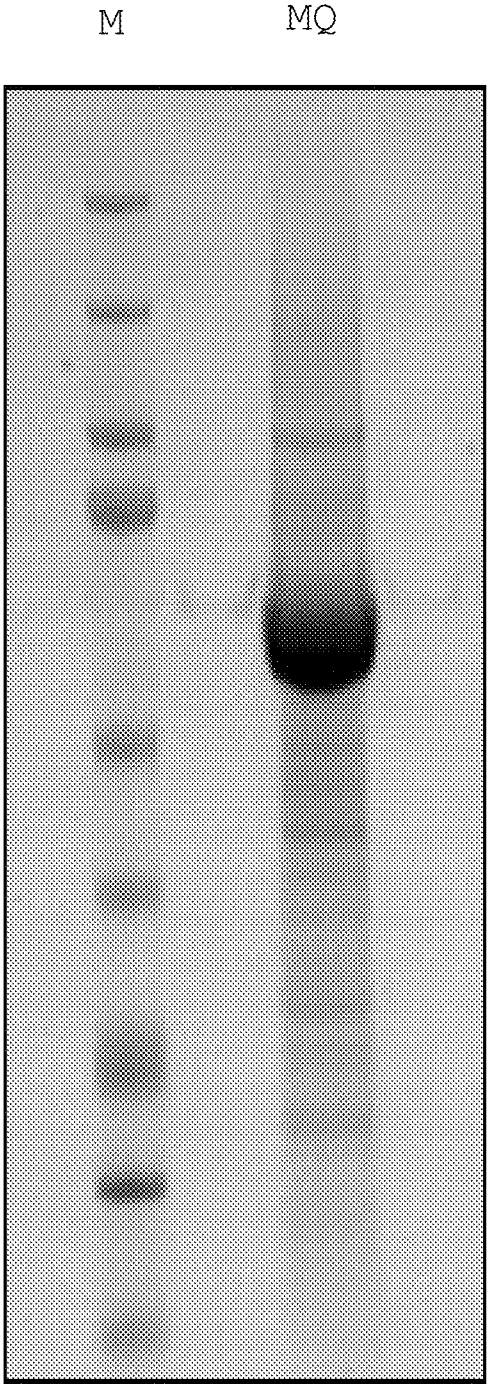
Figure 5:
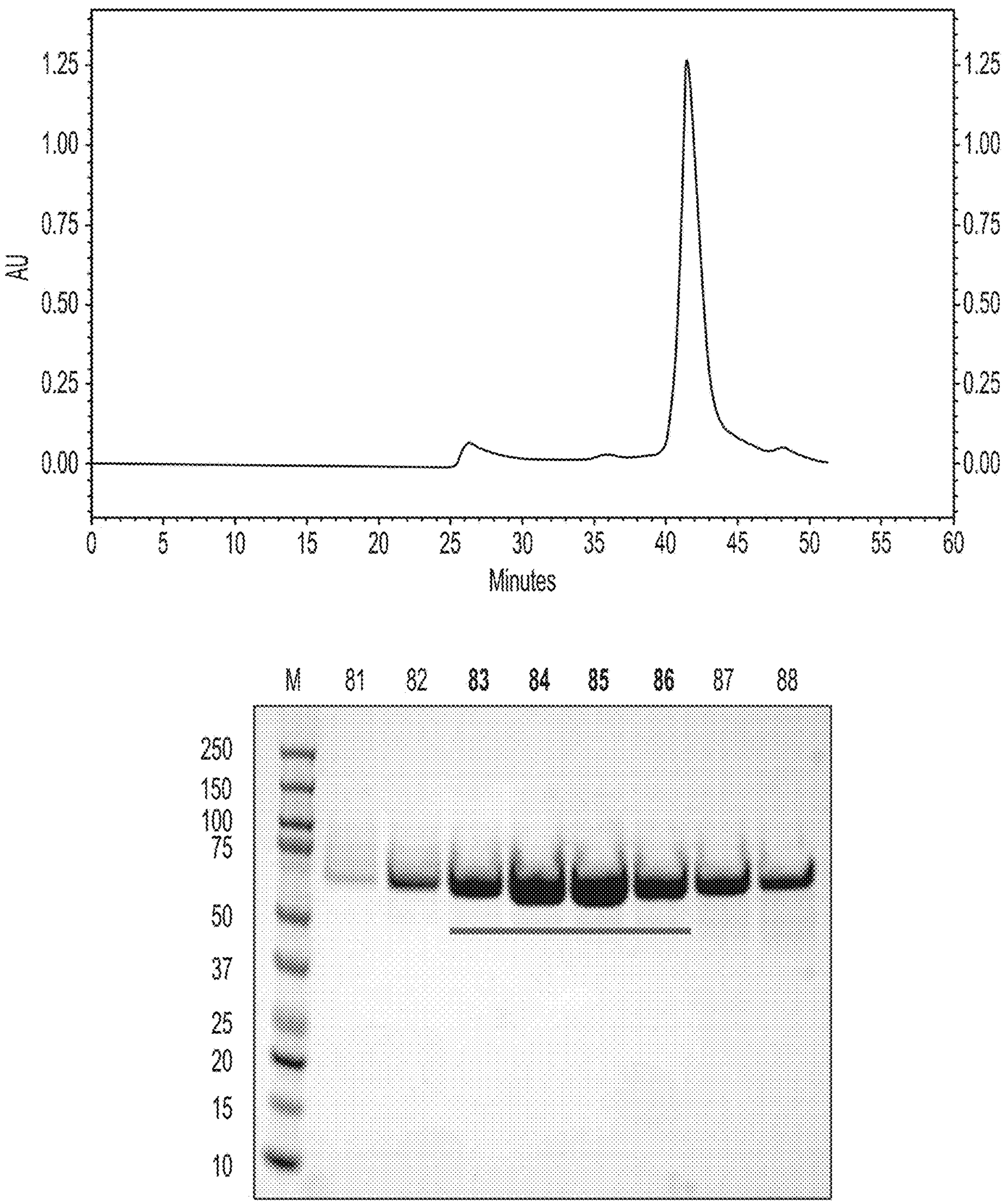
FIG. 5 shows representative chromatographic profile and Coomassie-stained SDS-PAGE gel of D2C7-IT TSK SEC fractions. Chromatographic profile of D2C7-IT eluate from the TSKgel SuperSW3000 column, D2C7-IT sample was injected into the TSK column and 30-second fractions (2 mL/min, total runtime 60 min) were collected and 30 μl of the D2C7-IT eluate fractions 81-88 from the TSK SEC column was analyzed in a SDS-PAGE gel. M: molecular weight standard.

To produce purified bulk lots of D2C7-IT, 12 rounds of seed buildup and fermentation (Fermentation Lot Numbers: 212011-212022) were performed using vials from the MCB. Each round of seed buildup and fermentation resulted in the generation of a new lot of cell paste, which were processed for inclusion body isolation. Multiple washes of the inclusion body isolation with Triton-X-100 detergent and Tris-EDTA buffer through centrifugation differentially removed a significant amount of contaminating host proteins as demonstrated in FIGS. 3A and 3B. The final inclusion body yield from each round of fermentation was in the range of 1.7-4.3 gms (Table I). The inclusion body pellets were solubilized in a strong denaturant (6 M Guanidine-HCl), reduced with DTE, and diluted 100-fold in the refolding buffer. Individual batches of refolded D2C7-1T protein (3-5 L refolding buffer) from each fermentation lot was dialyzed, filtered, and loaded onto Q-Sepharose FF anion exchange column. D2C7-IT protein bound to the Q-Sepharose column was eluted using a differential salt gradient and 5 ml fractions of the eluate was examined for purity in SDS-PAGE gel. Majority of the D2C7-IT was contained in 3-4 Q-Sepharose eluate fractions which were pooled for downstream processing. Representative D2C7-IT Q-Sepharose eluate fractions and the final purity of the combined Q-Sepharose fractions are shown in FIGS. 4A and 4B. The 1.7 gms of the inclusion body obtained from the first batch of D2C7-1T fermentation (Lot 212011) was purified through a total of six individual Q-Sepharose runs yielding a total of 86.3 mg of D2C7-IT. The pooled Q-Sepharose fractions were dialyzed in TSK buffer overnight at 4° C. for size exclusion chromatography purification. After overnight dialysis the protein was filtered and injected into TSKgel SuperSW3000 gel filtration column equilibrated with TSK buffer and the eluate corresponding to the major peak of D2C7-IT was analyzed in a SDS-PAGE gel. The fractions that contained only the D2C7-IT monomer (fractions 83-86 in FIG. 5) were pooled, concentrated, and loaded on to the ActiClean Etox column for endotoxin removal. The D2C7-IT eluate from the ActiClean Etox column was then dialyzed overnight at 4° C. against DPBS CTS. A total of nine batches of bulk lots of D2C7-IT (Lot No. 212032-212040) were purified with a total yield of 307.75 mg which were then transferred to 50 mL conical tubes, labeled, and stored at −80° C. A summary of the D2C7-IT purification process and the protein yields (Fermentation Lot No. 212032-212040 and TSK purified Bulk Lot No. 212032-212040) at each step has been summarized in Table I.

TABLE I

D2C7-TT purification process yield summary

| Fermentation | Lot 212011 | Lot 212012 | | Lot 212013 |
|---|---|---|---|---|
| Bacterial Culture | 8 L | 8 L | | 8 L |
| Total Inclusion Body | 1.7 g | 1.8 g | 2.4 g | 2.7 g |
| Refolding Volume | 17 L | 18 L | 24 L | 27 L |
| Pooled Q/S Fractions | 86.3 mg | 76.6 mg | 79. 1 mg | 116.5 mg |
| Dialysis and Filtration | 75.9 mg | 64.9 mg | 64.9 mg | 105.1 mg |
| Pooled TSK Fractions | 28.5 mg | 24.1 mg | 27.9 mg | 39.2 mg |
| Endotoxin Column | 28.4 mg | 23.9 mg | 21.3 mg | 40.9 mg |
| Dialysis vs PBS | 24.25 mg | 17.63 mg | 18.87 mg | 37.44 mg |
| Purified Bulk Number | Lot 212032 | Lot 212033 | Lot 212034 | Lot 212035 |

| Fermentation | Lot 212014 | Lot 212015 | Lot 212016 |
|---|---|---|---|
| Bacterial Culture | 8 L | 8 L | 8 L |
| Total Inclusion Body | 2.4 g | 2.8 g | 4.3 g |
| Refolding Volume | 24 L | 28 L | 4 or. |
| Pooled Q/S Fractions | 80.9 mg | 102.6 mg | 126.1 mg |
| Dialysis and Filtration | 70.25 mg | 88.7 mg | 100.5 mg |
| Pooled TSK Fractions | 30.7 mg | 50.4 mg | 56.3 mg |
| Endotoxin Column | 30.7 mg | 49.5 6 mg | 50.9 mg |
| Dialysis vs PBS | 29.81 mg | 42.60 mg | 51.69 mg |
| Purified Bulk Number | Lot 2120136 | Lot 212037 | Lot 212038 |

| Fermentation | Lot 212017 | Lot 212018 | Lot 212022 |
|---|---|---|---|
| Bacterial Culture | 8 L | 8 L | 8 L |
| Total Inclusion Body | 3.8 g | 1.7 g | 2.7 g |
| Refolding Volume | 38 L | 17 L | 27 L |
| Pooled Q/S Fractions | 144 mg | | 114.8 mg |
| Dialysis and Filtration | 114.3 mg | | 86.75 mg |
| Pooled TSK Fractions | 56.7 mg | | 42.4 mg |
| Endotoxin Column | 51.1 mg | | 45.2 mg |
| Dialysis vs PBS | 48.13 mg | | 37.33 mg |
| Purified Bulk Number | Lot 212039 | | Lot 212040 |

Example 4

Preparation of Final Purified Bulk D2C7-IT Product and Analytical Release Testing The final purified bulk D2C7-IT product was prepared by filtering and combining three batches of the intermediate bulk product, specifically Lot 212033, Lot 212034, and Lot 212035, for a total volume of 118 mL. The volume was adjusted to 250 mL by adding 132 mL of DPBS-CTS and the protein concentration was initially determined to be 0.36 mg/mL using the Pierce Coomassie Plus assay. However, during this initial assessment, the curve was not linear and therefore, the bulk product was further diluted to 500 mL by the addition of 250 ml DPBS-CTS. The protein concentration of the diluted pool was determined to be 0.166 mg/mL for a total of 83 mg of protein. The final volume was adjusted to 600 mL by adding 100 mL DPBS-CTS and the final concentration was determined to be 0.123 mg/mL. The final purified bulk D2C7-1T was designated as Lot 212041 and 20 1-mL vials were frozen and stored at −80° C. as the Purified Bulk reference standards. The purified bulk reference standard (D2C7-IT Lot 212041) was subjected to analytical release testing as described in materials and methods and the results are presented in Table II. The purified bulk D2C7-IT Lot 212041 was a colorless clear liquid with no particles at 25° C. The purified bulk D2C7-IT Lot 212041 generated a single band corresponding to 61 kDa and 62.5 kDa in a reduced and non-reduced SDS-PAGE analysis, respectively. The purified bulk D2C7-IT Lot 212041 had a final protein concentration of 0.123 mg/mL. The purified D2C7-IT Lot 212032 was used as reference standard for the assessment of cytotoxicity (IC50) of the purified bulk D2C7-IT Lot 212041. The cytotoxicity of the reference standard D2C7-IT Lot 212032 and purified bulk D2C7-IT Lot 212041 on mutant EGFRvIII expressing NR6M cells were 0.310 ng/mL and 0.410 ng/mL and on EGFRwt expressing A431P cells were 0.038 ng/mL and 0.049 ng/mL, respectively. The purified bulk D2C7-IT Lot 212041 had 98.7% monomers and 1.3% fragments by HPLC-SEC analysis. The isoelectric point of the purified bulk D2C7-IT Lot 212041 was 5.3. The purified bulk D2C7-IT Lot 212041 had pH of 7.4, DNA content of <20 pg/mL, endotoxin levels equivalent to 1.09 EU/mL, and exhibited no growth in sterility assay. The chloramphenicol content of Lot 212041 of the final purified bulk product was 1.2 µg/mL. According to the laboratory report from Toxicology Associates Inc., Columbus, Ohio, the levels of chloramphenicol in biological products needs to be >25 ng/mL to be toxic in humans. In the clinical study, we have proposed to infuse patients with a maximum of 1,143,504 ng of D2C7-IT, which is the equivalent to 9.53 mL of Lot 212041. Thus, the maximal potential exposure of chloramphenicol to patients in the clinical study will be 11.04 µg, which is below the toxic range of >25 µg/mL. Therefore, the levels of chloramphenicol in Lot 212041 were considered to be non-toxic. Additionally, the level of IPTG in Lot 212041 was undetectable as it was below the limit of sensitivity.

TABLE II

Purified bulk D2C74T Let 212041 analytical release testing summary
CERTIFICATE OF ANALYSIS
Product Name: D2C7-IT Purified Bulk Lot Number 212041 Production Date: Nov. 5, 2012
Lot Size: 20 vials Container Size/Fill volume: 2 mL/1 mL Storage Temperature: −80° C.
Description: D2C7-IT (scdsFv-PE38KDEL) is a dual specific single-chain dilsulfide-stabilized variable domain immunotoxin (containing *Pseudomonas* exotoxin) that targets both the epidermal growth factor receptor (EGFR) wild-type and tumor-specific variant form EGFRvIII. Colorless liquid in a solution of sterile PBS, pH 7.4.

| Test Description | Assay Specification | Results |
|---|---|---|
| Product Inspection | | |
| Color, Appearance and Clanty | Colorless, No Foreign matter, clear to slightly opalescent solution at 25° C. | Colorless, clear liquid with no particles @25° C. |
| Identity SDS-PAGE. Reduced & Non-reduced, Coomassie Blue Stain | Report major Bands, Conforms to Standard | Reduced: 1 band @61 kDa Non-reduced: 1 band @62.5 kDa Conforms to Std |
| Content | | |
| Protein Concentration by Pierce Coomassie Plus Assay | 0.12 ± 0.01 mg/mL | 0.123 mg/mL |
| Potency Cytotoxicity in NR6M & A431p cell lines | Conforms to Standard Lot 212032 | $IC_{50}$ values 212041 = 410 pg/mL @ NR6M 212041 = 49 pg/mL @ A431p Ref Std = 310 pg/mL @ NR6M Ref Std = 38 pg/mL @ A431p Conforms to Std |
| Purity | | |
| HPLC-SEC | ≥95% Total Protein, amounts of monomer, aggregates, & fragments | 98.7% Purity, 98.7% monomer 0% aggregates, 1.3% fragments |
| Gel IEF | Conforms to Standard | pl = 5.3 |
| Safety | | |
| DNA Content (*E. Coli*) | Report Results | <20 pg DNA/mL |
| Endotoxin (LAL) | ≤10 EU/mL | 1.09 EU/mL |
| Sterility | No growth | No Growth |
| pH | 7.4 ± 0.4 | 7.4 |

TABLE II-continued

| Purified bulk D2C74T Let 212041 analytical release testing summary<br>CERTIFICATE OF ANALYSIS<br>Product Name: D2C7-IT Purified Bulk Lot Number 212041 Production Date: Nov. 5, 2012<br>Lot Size: 20 vials Container Size/Fill volume: 2 mL/1 mL Storage Temperature: −80° C.<br>Description: D2C7-IT (scdsFv-PE38KDEL) is a dual specific single-chain dilsulfide-stabilized variable domain immunotoxin (containing *Pseudomonas* exotoxin) that targets both the epidermal growth factor receptor (EGFR) wild-type and tumor-specific variant form EGFRvIII. Colorless liquid in a solution of sterile PBS, pH 7.4. | | |
|---|---|---|
| Test Description | Assay Specification | Results |
| Chloramphenicol | Report Results | 1.2 μg/mL |
| Isopropyl-β-D-1-thiogalactopyran-oside Content | Report Results | <50 ng/mL, Limit of sensitivity. Not detected |

Example 5

Preparation of Final Vialed D2C7-JT Product and Analytical Release Testing

Upon clearance of the analytical release testing the remaining 580 mL of the purified bulk D2C7-JT Lot 212041 was sent to the Compounding Pharmacy at Duke University Medical Center for vialing. The final product contained approximately 1 mL of purified D2C7-IT/vial at a concentration of 120 μg/mL in DPBS-CTS. A total of 560 vials labelled as Lot 211131 were prepared and delivered, which were and stored at <−70° C. The final vialed product, D2C7-IT Lot 211131, underwent similar analytical release testing as the final purified bulk product with the exception of assessment for DNA, chloramphenicol, and IPTG content, since these tests have already been performed. The analytical release testing results for the final vialed product, D2C7-IT Lot 211131 is presented in Table III. The final vialed D2C7-IT Lot 211131 was a colorless clear liquid with no particles at 25° C. The final vialed D2C7-IT Lot 211131 generated a single band corresponding to 61 kDa and 62.5 kDa in a reduced and non-reduced SDS-PAGE analysis, respectively. The final vialed D2C7-IT Lot 211131 had a final protein concentration of 0.12 mg/mL. The purified D2C7-IT Lot 212032 was used as reference standard for the assessment of cytotoxicity ($IC_{50}$) of the final vialed D2C7-IT Lot 211131. The cytotoxicity of the reference standard D2C7-IT Lot 212032 and final vialed D2C7-IT Lot 211131 on mutant EGFRvIII expressing NR6M cells were 0.210 ng/mL and 0.120 ng/mL and on EGFRwt expressing A431P cells were 0.031 ng/mL and 0.041 ng/mL, respectively. The final vialed D2C7-IT Lot 211131 had 97.7% monomers and 2.1% fragments by HPLC-SEC analysis. The isoelectric point of the final vialed D2C7-IT Lot 211131 was 5.3. The final vialed D2C7-IT Lot 211131 had pH of 7.4, endotoxin levels equivalent to 1.26 EU/mL, and exhibited no growth in sterility assay.

TABLE III

| Final vialed D2C7-IT Lot 21113 1 analytical release testing summary<br>CERTIFICATE OF ANALYSIS<br>Product Name: D2C7-IT Final Vialed Product Lot Number: 211131<br>Production Date: Nov. 7, 2012<br>Lot Size: 560 vials Container Size/Fill volume: 2 mL/1 mL Storage Temperature: −80° C.<br>Description: D2C7-IT (scdsFv-PE38KDEL) to a dual specific single-chain disulfide-stabilized variable domain immunotoxin (containing *Pseudomonas* exotoxin) that targets both the epidermal growth factor receptor (EGFR) wild-type and tumor-specific variant form EGFRvIII. Colorless liquid in a solution of sterile PBS, pH 7.4. | | |
|---|---|---|
| Test Description | Assay Specification | Results |
| Product Inspection | | |
| Color, Appearance and Clarity | Colorless, No Foreign matter, clear to slightly opalescent solution at 25° C. | Colorless, clear liquid. Free from particles @25° C. |
| Identity<br>SDS-PAGE, Reduced & Non-reduced, Coomassie Blue Stain | Report Major Bands. Conforms to Standard | Reduced:<br>1 band @61 kDa<br>Non-reduced:<br>1 band @62.5 kDa<br>Conforms to Std |
| Content | | |
| Protein Concentration by Pierce Coomassie Plus Assay | 0.12 ± 0.01 mg/mL | 0.12 mg/mL |
| Potency<br>Cytotoxicity in NR6M & A431p cell lines | Conforms to Standard | $IC_{50}$ values<br>211131 = 120 pg/mL @ NR6M<br>211131 = 41 pg/mL @ A431p<br>Ref Std = 210 pg/mL @ NR6M<br>Ref Std = 31 pg/mL @ A431p<br>Conforms to Std |

TABLE III-continued

| Final vialed D2C7-IT Lot 21113 1 analytical release testing summary CERTIFICATE OF ANALYSIS Product Name: D2C7-IT Final Vialed Product Lot Number: 211131 Production Date: Nov. 7, 2012 Lot Size: 560 vials Container Size/Fill volume: 2 mL/1 mL Storage Temperature: −80° C. Description: D2C7-IT (scdsFv-PE38KDEL) to a dual specific single-chain disulfide-stabilized variable domain immunotoxin (containing *Pseudomonas* exotoxin) that targets both the epidermal growth factor receptor (EGFR) wild-type and tumor-specific variant form EGFRvIII. Colorless liquid in a solution of sterile PBS, pH 7.4. | | |
|---|---|---|
| Test Description | Assay Specification | Results |
| Purity | | |
| HPLC-SEC | ≥95% Total Protein, amounts of monomer, aggregates, & fragments | 97.7% Purify, 97.7% monomer 0% aggregates. 2.1% fragments |
| Gel IEF | Conforms to Standard | pl = 5.3 |
| Safety | | |
| Endotoxtn (LAL) | ≤10 EU/mL | 1.26 EU/mL |
| Sterility | No growth | No Growth |
| pH | 7.4 ± 0.4 | 7.4 |

Example 6

Stability Testing of Final Vialed Product D2C7-IT Lot 211131

Stability testing of the final vialed product, D2C7-IT Lot 211131 is being conducted over 5-year duration, from November 2012 to November 2017 by DUMC/AEAT program. Visual appearance, protein concentration, purity, potency, and pH are being assessed by the methods outlined in materials and methods section and will be tested at 0, 3, 6, 9, 12, 18, 24, 30, 36, 42, 48, 54, and 60 month time points. Sterility testing will be performed annually. Specifications for each of the stability tests have been determined and are as follows: 1) the visual appearance specification requires that the results are clear with no foreign matter, 2) the protein concentration by Pierce Coomassie Plus used to determine protein content specifies a range of 0.12 mg/mL+0.01 mg/mL, 3) the major bands and that the banding pattern reported by SDS-PAGE conforms to the standard (reference standard lot 212041), 4) the results reported by IEF gel conforms to the standard, 5) purity results as determined by HPLC-SEC must meet a specification of >95% total protein amounts of monomer, 6) the results of the cytotoxicity assay used to determine the potency of the product must conform to the standard (reference standard Lot 212041), 7) the product must be found sterile, and 8) the acceptable pH range is 7.4±0.4. The stability tests performed, the assay specifications, and the available test results are summarized in Table IV. The results indicated that Lot 211131 of the final vialed product met the specifications set for the required assays through 42 months.

TABLE IV

| Stability Results for D2C7-IT, Lot 211131, Time 0 through 5 Years - Continued Production Date: Nov. 7, 2012 | | | | | | | |
|---|---|---|---|---|---|---|---|
| | | Time Point | | | | | |
| Test | Specification | 0 Month November 2012 | 3 Months Feb. 3, 2013 | 6 Months May 6, 2013 | 9 Months Aug. 9, 2013 | 12-14 Months December 2013-February 2014 | 18 Months May 6, 2014 |
| Appearance | Colorless, Clear, No particles or precipitation | Colorless, clear solution | Colorless, clear liquid. Free from particles | Colorless, clear solution with no particles | Colorless, clear liquid with no particles | Colorless, clear liquid with no particles | Colorless, clear liquid with no particles |
| Content Protein Conc. by Pierce Coomassie Plus Assay | 0.12 ± 0.01 mg/mL | 0.12 mg/mL | NA | NA | 0.121 mg/mL | 0.117 mg/mL | 0.123 mg/mL |
| SDS-PAGE, Reduced & Non-reduced, Coomassie Blue Stain | Report Major Bands, Conforms to Standard* | Non-reduced: 1 band @62.5 kDa Conforms to Std | Non-reduced: 1 band @62.5 kDa Conforms to Std | Non-reduced: 1 band @62 kDa Conforms to Std | Reduced: 1 band @61 kDa Non-reduced: 1 band @62.5 kDa Conforms to Std | Reduced: 1 band @61.5 kDa Non-reduced: 1 band @63.3 kDa Conforms to Std | Reduced: 1 band @63.1 kDa Non-reduced: 1 band @62.9 kDa Conforms to Std |
| Gel IEF | Conforms to Standard* | 5.3 | NA | NA | 5.3 | 5.3 | 5.3 |

TABLE IV-continued

Stability Results for D2C7-IT, Lot 211131, Time 0 through 5 Years - Continued Production Date: Nov. 7, 2012

| | | | | | | | |
|---|---|---|---|---|---|---|---|
| Purity HPLC-SEC | ≥95% monomer | 97.7% Purity 97.7% monomer 0% aggregates 2.1% fragments | NA | NA | 99.87% Purity 99.86% monomer 0% aggregates 0.138% fragments | 98.8% Purity 98.8% monomer 0% aggregates 1.1% fragments | 100% Purity 100% monomer 0% aggregates 0% fragments |
| Potency Cytotoxicity in NR6M & A431p cell lines | Conforms to Reference Standard** Lot 212041 (Relative Activity %) | $IC_{50}$ values 211131 = 120 pg/mL @ NR6M (175%) Ref Std = 210 pg/mL @ NR6M (100%) 211131 = 41 pg/mL @ A431p (76%) Ref Std = 31 pg/mL @ A431p (100%) Conforms to Std | $IC_{50}$ values 211131 = 400 pg/mL @ NR6M 211131 = 42 pg/mL @ A431p Conforms to Std | $IC_{50}$ values 211131 = 410 pg/mL @ NR6M 211131 = 41 pg/mL @ A431p Conforms to Std | $IC_{50}$ values 211131 = 390 pg/mL @ NR6M (105%) Ref Std = 410 pg/mL @ NR6M (100%) 211131 = 51 pg/mL @ A431p (96%) Ref Std = 49 pg/mL @ A431p (100%) Conforms to Std | $IC_{50}$ values 211131 = 400 pg/mL @ NR6M (100%) Ref Std = 400 pg/mL @ NR6M (100%) 211131 = 39 pg/mL @ A431p (105%) Ref Std = 41 pg/mL @ A431p (100%) Conforms to Std | $IC_{50}$ values 211131 = 205 pg/mL @ NR6M (100%) Ref Std = 205 pg/mL @ NR6M (100%) 211131 = 36 pg/mL @ A431p (108%) Ref Std = 39 pg/mL @ A431p (100%) Conforms to Std |
| Sterility | No Growth | No Growth | Not Required | Not Required | Not Required | No Growth | Not Required |
| pH | 7.4 ± 0.4 | 7.4 | NA | NA | 7.4 | 7.4 | 7.4 |

| | | Time Point | | | | | |
|---|---|---|---|---|---|---|---|
| Test | Specification | 24 Months Nov. 12, 2014 | 30 Months May 6, 2015 | 36 Months January 2016 | 42 Months May 6, 2016 | 48 Months Nov. 12, 2016 | 54 Months May 6, 2017 |
| Appearance | Colorless, Clear, No particles or precipitation | Colorless, Clear, No particles or precipitation | Colorless, Clear, No particles or precipitation | Colorless, Clear, No particles or precipitation | Colorless, Clear, No particles or precipitation | | |
| Content Protein Conc. by Pierce Coomassie Plus Assay | 0.12 ± 0.01 mg/mL | 0.112 mg/mL | 0.118 mg/mL | 0.125 mg/mL | 0.122 mg/mL | | |
| SDS-PAGE, Reducing & Non-reduced, Coomassie Stain with Densitometry | Report Major Bands, Conforms to Standard* | Reduced: 1 band @ 63.2 kDa Non-reduced: 1 band @ 60.2 kDa Conforms to Std | Reduced: 1 band @ 66.2 kDa Non-reduced: 1 band @ 62.55 kDa Conforms to Std | Reduced: 1 band @ 63.4 kDa Non-reduced: 1 band @ 60.55 kDa Conforms to Std | Reduced: 1 band @ 66.65 kDa Non-reduced: 1 band @ 61.35 kDa Conforms to Std | | |
| Gel IEF | Conforms to Standard* | 5.3 | 5.3 | 5.3 | 5.3 | | |
| Purity HPLC-SEC | ≥95% monomer | 97.4% Purity 97.4% monomer 0.95% aggregates 1.67% fragments | 98.213% Purity 98.213% monomer 0% aggregates 1.787% fragments | 98.150% Purity 98.150% monomer 1.850% aggregates 0% fragments | 96.442% Purity 96.442% monomer 0% aggregates 3.558% fragments | | |
| Potency Cytotoxicity in NR6M & A431p cell lines | Conforms to Reference Standard** Lot 212041 (Relative Activity %) | $IC_{50}$ values 211131 = 290 pg/mL @ NR6M (100%) Ref Std = 290 pg/mL @ NR6M (100%) 211131 = 48 pg/mL @ A431p (125%) Ref Std = 60 pg/mL @ A431p (100%) Conforms to Std | $IC_{50}$ values 211131 = 300 pg/mL @ NR6M (77%) Ref Std = 230 pg/mL @ NR6M (100%) 211131 = 21 pg/mL @ A431p (100%) Ref Std = 21 pg/mL @ A431p (100%) Conforms to Std | $IC_{50}$ values 211131 = 460 pg/mL @ NR6M (100%) Ref Std = 460 pg/mL @ NR6M (100%) 211131 = 23 pg/mL @ A431p (122%) Ref Std = 28 pg/mL @ A431p (100%) Conforms to Std | $IC_{50}$ values 211131 = 230 pg/mL @ NR6M (100%) Ref Std = 300 pg/mL @ NR6M (100%) 211131 = 50 pg/mL @ A431p (122%) Ref Std = 61 pg/mL @ A431p (100%) Conforms to Std | | |

TABLE IV-continued

| Stability Results for D2C7-IT, Lot 211131, Time 0 through 5 Years - Continued Production Date: Nov. 7, 2012 | | | | | |
|---|---|---|---|---|---|
| Sterility | No Growth | No Growth | Not Required | No Growth | Not Required |
| pH | 7.4 ± 0.4 | 7.39 | 7.2 | 7.18 | 7.23 |

*"Conforms to Standard": there are no new bands as compared to reference standard, and the relative percentage of each species remains constant.

**The revised acceptance criteria values for future DS (lot 212041) and DP (lot 211131) stability and intermediate bulk lot stability on A431p and NR6M cells are as follows: 1. NR6M cells: DS (Reference Standard) 306.3 ± 114.1 pg/ml [192.2-420.4 pg/ml]; DP 432.9 ± 161.4 pg/ml [271.5-594.3 pg/ml] 2. A431p cells: DS (Reference Standard) 40 ± 7.39 pg/ml [32.6-47.4 pg/ml]; DP 40.35 ± 14.26 pg/ml [26.1-54.6 pg/ml]

REFERENCES

The disclosure of each reference cited is expressly incorporated herein.

1. Rubin Grandis, J., et al., Quantitative immunohistochemical analysis of transforming growth factor-alpha and epidermal growth factor receptor in patients with squamous cell carcinoma of the head and neck Cancer, 1996. 78(6): p. 1284-92.
2. Klijn, J. G., et al., The clinical significance of epidermal growth factor receptor (EGF-R) in human breast cancer: a review on 5232 patients. Endocr Rev, 1992.13(1): p. 3-17.
3. Bartlett, J. M., et al., The prognostic value of epidermal growth factor receptor mRNA expression in primary ovarian cancer. Br J Cancer, 1996. 73(3): p. 301-6.
4. Pavelic, K., et al., Evidence for a role of EGF receptor in the progression of human lung carcinoma. Anticancer Res, 1993. 13(4): p. 1133-7.
5. Fox, S. B., et al., Prognostic value of c-erbB-2 and epidermal growth factor receptor in stage A1 (Tla) prostatic adenocarcinoma. Br J Urol, 1994. 74(2): p. 214-20.
6. Arita, N., et al., Epidermal growth factor receptor in human glioma. J Neurosurg, 1989. 70(6): p. 916-9.
7. Libermann, T. A., et al., Expression of epidermal growth factor receptors in human brain tumors. Cancer Res, 1984. 44(2): p. 753-60.
8. Libermann, T. A., et al., Amplification, enhanced expression and possible rearrangement of EGF receptor gene in primary human brain tumours of glial origin. Nature, 1985. 313(5998): p. 144-7.
9. Brennan, C. W., et al., The somatic genomic landscape of glioblastoma. Cell, 2013. 155(2): p. 462-77.
10. Chaffanet, M., et al., EGF receptor amplification and expression in human brain tumours. Eur J Cancer, 1992. 28(1): p. 11-7.
11. Frederick, L., et al., Diversity and frequency of epidermal growth factor receptor mutations in human glioblastomas. Cancer Res, 2000. 60(5): p. 1383-7.
12. Weldon, J. E. and I. Pastan, A guide to taming a toxin-recombinant immunotoxins constructed from *Pseudomonas* exotoxin A for the treatment of cancer. FEBS J, 2011. 278(23): p. 4683-700.
13. Seetharam, S., et al., Increased cytotoxic activity of *Pseudomonas* exotoxin and two chimeric toxins ending in KDEL. J Biol Chem, 1991. 266(26): p. 17376-81.
14. Chandramohan, V., et al., Construction of an immunotoxin, D2C7-(scdsFv)-PE3 8KDEL, targeting EGFRwt and EGFRvIII for brain tumor therapy. Clin Cancer Res, 2013. 19(17): p. 4717-27.

The invention claimed is:

1. A method of producing clinical grade D2C7(scdsFv)-PE38KDEL immunotoxin, comprising the steps of:

a. culturing an *E. coli* BLR (λ, DE3) lambda lysogen comprising a plasmid encoding said immunotoxin in a fermentor to produce a bacterial cell paste, the expression of said immunotoxin was under the control of the T7 promoter and induced with Isopropyl β-D-1-thiogalactopyranoside;

b. lysing bacteria of the bacterial cell paste in a buffer comprising $MgSO_4$, DNaseI, and lysozyme;

c. collecting inclusion bodies from the lysed bacteria;

d. solubilizing the inclusion bodies and reducing proteins of the solubilized inclusion bodies to form reduced proteins of the inclusion bodies;

e. refolding the reduced proteins of the inclusion bodies in the presence of a protease inhibitor to form single-chain disulfide stabilized immunotoxin;

f. purifying the single-chain disulfide stabilized immunotoxin to remove the protease inhibitor and endotoxin; to form purified, single-chain disulfide stabilized immunotoxin; and g. storing the purified single-chain disulfide stabilized immunotoxin at a temperature of −70° to −90° C.

2. The method of claim 1 wherein the *E. coli* lambda lysogen is made by transforming competent cells of an *E. coli* lambda lysogen with a plasmid encoding said immunotoxin, and recovering a transformant.

3. The method of claim 1 wherein the step of purifying comprises anion-exchange chromatography.

4. The method of claim 1 wherein the step of purifying comprises size exclusion chromatography.

5. The method of claim 1 wherein the step of purifying comprises anion-exchange chromatography and size exclusion chromatography.

6. The method of claim 1 wherein intermediate purification products are stored at −70° to −90° C.

* * * * *